United States Patent [19]

Franz et al.

[11] Patent Number: 5,410,070
[45] Date of Patent: Apr. 25, 1995

[54] PREPARATION OF N-ALKENYLPYRROLIDONES

[75] Inventors: Lothar Franz, Mutterstadt; Michael Huellmann, Heppenheim, both of Germany

[73] Assignee: BASF Aktiengesellschaft, Ludwigshafen, Germany

[21] Appl. No.: 188,206

[22] Filed: Jan. 27, 1994

[30] Foreign Application Priority Data

Jan. 28, 1993 [DE] Germany .................. 43 02 325.8

[51] Int. Cl.⁶ .......................................... C07D 207/26
[52] U.S. Cl. ............................... 548/552; 548/543
[58] Field of Search .............................. 548/543, 552

[56] References Cited

U.S. PATENT DOCUMENTS

| | | | |
|---|---|---|---|
| 2,669,570 | 2/1954 | Schnizer | 260/326.5 |
| 3,377,340 | 4/1963 | Hartwimmer et al. | 260/239.3 |
| 3,526,620 | 9/1970 | Bestian et al. | 260/239.3 |
| 3,821,245 | 6/1974 | Kanetaka et al. | 260/326.5 FM |

OTHER PUBLICATIONS

Chemical Abstracts, vol. 79, No. 11, 17. Sep. 1973, abstract No. 66172v.
Chemische Berichte, Bohme et al, Jul. 1966, Weinheim de Seiten 2127-2135.
Izv. Akad. SSSR, (1961) 901–905.

*Primary Examiner*—David B. Springer
*Attorney, Agent, or Firm*—John H. Shurtleff

[57] ABSTRACT

Process for the preparation of N-alkenylpyrrolidones of the general formula

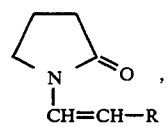

(I)

in which R denotes hydrogen or $C_1$–$C_{20}$alkyl, by the reaction of an N-alkylpyrrolidone of the general formula

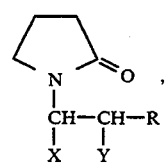

(II)

in which R has the aforementioned meanings, and x and Y stand for OH, $C_1$–$C_{20}$alkoxy or $C_2$–$C_{20}$alkoxycarbonyl, provided that one of the two radicals x and denotes hydrogen, at temperatures ranging from 200° to 600° C. and pressures ranging from 0.1 to 5 bar, wherein the process is carried out in the presence of an acid heterogenous catalyst except for an oxide of a Group IIb, Group IIIb, Group IVb, and Group VIb metal.

10 Claims, No Drawings

PREPARATION OF N-ALKENYLPYRROLIDONES

The present invention relates to a process for the preparation of N-alkenylpyrrolidones by the reaction of N-alkylpyrrolidones at elevated temperatures over acid heterogenous catalysts, except for oxides of Group IIb, Group IIIb, Group IVb, and Group VIb metals.

DE-A2,135,211 describes a process for the preparation of N-vinylpyrrolidone by the reaction of N-(2-hydroxyethyl)-2-pyrrolidone in contact with catalysts of oxides of Group IIb, Group IIIb, Group IVb, and Group VIb metals under atmospheric pressure and at temperatures ranging from 250° to 500° C. in the gas phase. A disadvantage of this process is the side reaction causing the formation of 2-pyrrolidone, which is in some cases extensive.

According to U.S. Pat. No. 2,669,570 N-vinylpyrrolidone can be prepared from N-(2-hydroxy)-vinylpyrrolidone using basic or neutral aluminum oxide at temperatures ranging from 290° to 335° C. by the elimination of water in the gas phase at pressures below 100 mm of Hg. Furthermore, said reference states that the elimination of water from N-hydroxyethylpyrrolidones can be carried out in the gas phase over Broensted acid catalysts, particularly phosphoric acid catalysts, only with extensive destruction of the starting material.

The uncatalyzed acetous pyrolysis of N-(2-acetoxyethyl)-pyrrolidone described in *Izv. Akad. SSSR*, (1961)901 to 905 shows that only moderate yields are obtained under these conditions.

It is thus an object of the present invention to overcome the aforementioned drawbacks.

Accordingly, we have found a novel and improved process for the preparation of N-alkenylpyrrolidones of the general formula I

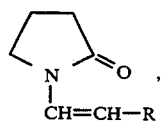

in which R denotes hydrogen or $C_1$–$C_{20}$alkyl, by the reaction of N-alkylpyrrolidones of the general formula II

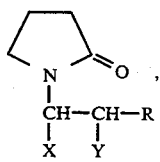

in which R has the aforementioned meanings, and x and Y stand for OH, $C_1$–$C_{20}$alkoxy or $C_2$–$C_{20}$alkoxycarbonyl, provided that one of the two radicals x and Y denotes hydrogen, at temperatures ranging from 200° to 600° C. and pressures ranging from 0.1 to 5 bar, wherein the process is carried out in the presence of acid heterogenous catalysts except for oxides of Group IIb, Group IIIb, Group IVb, and Group VIb metals.

The process of the invention can be carried out as follows:

The N-alkylpyrrolidones II can be contacted at temperatures ranging from 200° to 600° C. and preferably from 250° to 500° C. and more preferably from 280° to 480° C. and pressures ranging from 0.1 to 5 bar and preferably from 0.2 to 2.5 bar and more preferably from 0.5 to 1.5 bar with acid heterogenous catalysts, except for oxides of Group IIb, Group IIIb, Group IVb, and Group VIb metals. The N-alkylpyrrolidones II are usually passed over the catalysts in the vaporous state, whilst the addition of inert gases, such as hydrogen, nitrogen, and steam, or the addition of inert organic solvents, or the use of reduced pressure can be advantageous.

Suitable acid heterogenous catalysts, except for oxides of Group IIb, Group IIIb, Group IVb, and Group VIb metals, are oxides of Group IIIA and Group IVa elements and/or phosphorous compounds on supports and/or molecular sieves.

Suitable molecular sieves are those having a laminated structure such as montmorillonites, kaolinites, and bentonites or those having a hollow structure such as zeolites, preferably in the H-form.

Suitable oxides of Group IIIa and Group IVa elements are oxides of boron, aluminum, gallium, indium, silicon, germanium, tin and lead.

Suitable phosphorous compounds are phosphorous acids such as orthophosphorous acids, phosphoric acid such as orthophosphoric acid, pyrophosphoric acid, metaphosphoric acid and condensed phosphoric acids such as polyphosphoric acid, their anhydrides and their salts of Group Ia, Group IIa, Group IIIa, Group IVa, and Group Va elements or of Group Ib, Group IIb, Group IIIb, Group Vb, Group VIb, Group VIIb, and Group VIIIb elements or of the lanthanides such as phosphates, pyrophosphates, monohydrogen phosphates, and dihydrogen phosphates, alkyl or aryl esters of phosphoric acid or phosphorous acid or alkyl-substituted or aryl-substituted phosphoric acid or phosphorous acid preferably on inert supports.

Lithium, sodium, potassium, rubidium, and cesium salts may be mentioned as salts of Group Ia elements, beryllium, magnesium, calcium, strontium, and barium salts as salts of Group IIa elements, boron, aluminum, gallium, indium, and thallium salts as salts of Group IIIa elements, titanium, zirconium, and hafnium salts as salts of Group IVa elements, ammonium, antimony, and bismuth salts as salts of Group Va elements, copper salts as salts of Group Ib elements, zinc, cadmium, and mercury salts as salts of Group IIb elements, scandium, yttrium, and lanthanum salts as salts of Group IIb elements, vanadium, niobium, and tantalum salts as salts of Group Vb elements, chromium salts as salts of Group VIb elements, manganese salts as salts of Group VIIb elements, iron, cobalt, and nickel salts as salts of Group VIII elements, and cerium, praseodymium, neodymium, promethium, samarium, europium, gadolinium, terbium, dysprosium, holmium, erbium, thulium, ytterbium, and lutetium salts as salts of the lanthanides, said salts being phosphates, pyrophosphates, monohydrogen phosphates, and preferably dihydrogen phosphates.

Suitable alkyl or aryl esters of phosphoric acid or phosphorous acid are mono-, di-or tri-esters having from I to 8 carbon atoms per alkyl radical such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, and n-hexyl or aryl groups such as phenyl, 1-naphthyl, 2-naphthyl, 1-anthryl, 2-anthryl, and 9-anthryl and preferably phenyl, 1-naphthyl, and 2-naphthyl and more preferably phenyl or $C_1$–$C_8$alkyl-substituted phenyl, for example, triethyl phosphate, triethyl phosphite, phenyl phosphate or phenyl phosphite.

Suitable alkyl-substituted or aryl-substituted phosphoric acid or phosphorous acid contain as substituents $C_1$–$C_8$alkyl preferably $C_1C_4$alkyl such as methyl, ethyl, n-propyl, isopropyl, n-butyl, isobutyl, sec-butyl, and tert-butyl or aryl such as phenyl, 1-naphthyl, 2-naphthyl, 1-anthryl, 2-anthryl, and 9-anthryl and preferably phenyl, 1-naphthyl, and 2-naphthyl and more preferably phenyl, examples being phenylphosphinic acid, ethylphosphinic acid, phenylphosphonic acid and naphthylphosphonic acid.

Particularly preferred representatives of the aforementioned phosphorous compounds are the dihydrogen phosphates, the hydrogen phosphates of Group IIa elements, the phosphates of vanadium and the lanthanides.

Suitable inert supports are, for example, aluminum oxides, silicon dioxide, titanium dioxide, and zeolites and mixtures thereof and clay.

The substituents R, X, and Y in the compounds I and II have the following meanings:

R hydrogen or $C_1$–$C_{20}$alkyl and preferably $C_1$–$C_8$alkyl such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, n-hexyl, isohexyl, sec-hexyl, n-heptyl, isoheptyl, n-octyl, isooctyl and more preferably $C_1$–$C_4$alkyl such as methyl, ethyl, n-propyl, isopropyl, n-butyl, isobutyl, sec-butyl, and tert-butyl, x and Y hydroxy, $C_2$–$C_{20}$alkoxy and preferably $C$–$C_8$alkoxy such as methoxy, ethoxy, n-propoxy, isopropoxy, n-butoxy, isobutoxy, sec-butoxy, tert-butoxy, n-pentoxy, isopentoxy, sec-pentoxy, neopentoxy, 1,2-dimethylpropoxy, n-hexoxy, isohexoxy, sec-hexoxy, n-heptoxy, isoheptoxy, n-octoxy, isooctoxy and more preferably $C$–$C_4$alkoxy such as methoxy, ethoxy, n-propoxy, isopropoxy, n-butoxy, isobutoxy, sec-butoxy, and tert- butoxy or $C_2$–$C_2$alkoxycarbonyl and preferably $C_2$–$C_9$alkoxycarbonyl such as methoxycarbonyl, ethoxycarbonyl, n-propoxycarbonyl, isopropoxycarbonyl, n-butoxycarbonyl, isobutoxycarbonyl, sec-butoxycarbonyl, tert-butoxycarbonyl, n-pentoxycarbonyl, isopentoxycarbonyl, sec-pentoxycarbonyl, neopentoxycarbonyl, 1,2 -dimethylpropoxycarbonyl, n-hexoxycarbonyl, isohexoxycarbonyl, sec-hexoxycarbonyl, n-heptoxycarbonyl, isoheptoxycarbonyl, n-octoxycarbonyl, isooctoxycarbonyl and more preferably $C_2$–$C_5$alkoxycarbonyl such as methoxycarbonyl, ethoxycarbonyl, n-propoxycarbonyl, isopropoxycarbonyl, n-butoxycarbonyl, isobutoxycarbonyl, sec-butoxycarbonyl, and tert-butoxycarbonyl, provided that one of the two radicals x and Y denotes hydrogen.

One special advantage of the invention resides in the fact that it provides simple and economical preparation of the catalysts coupled with easy reactivation thereof.

The N-alkenylpyrrolidones [are suitable as intermediates.

EXAMPLE

Example 1

Preparation of $SiO_2$ Impregnated with Phosphoric Acid 330 g of 75% strength phosphoric acid is poured into a vessel with water until the total volume of the mixture is 860 mL. This solution is then added to 490 g of $SiO_2$ and the suspension is mixed in a drum for 15 min. Following filtration, the residues are first of all subjected to heat treatment for 64 h at a temperature of 120° C., and then calcined for 3 h at 250° C.

Example 2

Preparation of Catalyst/$La(H_2PO_4)_3$ 168 g of diatomaceous earth and 449.5 g of a 20% strength aqueous solution of ammonium dihydrogen phosphate were added to 112.8 g of lanthanum nitrate×6 $H_2O$ dissolved in 300 mL of water, with stirring. The solution was heated, the water evaporated off, and the residues were dried for 3 h at 120° C. and then heated for a period of 3 h at a temperature of 400° C. bei.

Example 3

An electrically heated quartz tube having a length of 150 cm and an internal diameter of 30 mm was used as reactor, the lower portion thereof being packed with 225 mL of catalyst. The temperature in the reactor could be measured by means of a thermocouple displaceable in the longitudinal axis. The head of the column carried a dripping funnel for the educt II. The bottom end of the furnace was connected to a flask, equipped with a reflux condenser for the purpose of condensing the effluent hot gas mixture. In order to separate very volatile portions from the stream of gas, a cold trap cooled with dry ice/acetone was installed down stream. The operation and the yields and selectivities are listed in Table 1 below.

TABLE 1

| Name of Educt II | Cat. | Dilution with $N_2$ | Pressure [mbar] | Temp. [°C.] | Throughput [L/L.h] | Conv. [%] | Selectivity [%] |
| --- | --- | --- | --- | --- | --- | --- | --- |
| N-(3-hydroxypropyl)-pyrrolidone | Example 1 | — | 50 | 320 | 0.65 | 82 | 92 |
| N-(3-methoxypropyl)-pyrrolidone | Example 1 | — | 50 | 340 | 0.65 | 94 | 90 |
| N-(3-methoxypropyl)-pyrrolidone | Example 1 | — | 1000 | 340 | 0.3 | 70 | 90 |
| N-(2-hydroxyethyl)-pyrrolidone | Example 1 | — | 50 | 330 | 0.45 | 56 | 84 |
| N-(2-hydroxyethyl)-pyrrolidone | Example 1 | — | 50 | 345 | 0.50 | 40 | 90 |
| N-(2-hydroxyethyl)-pyrrolidone | Example 2 | — | 50 | 320 | 0.30 | 35 | 80 |
| N-(2-hydroxyethyl)-pyrrolidone | Example 2 | — | 50 | 350 | 0.30 | 80 | 90 |

We claim:

1. A process for the preparation of an N-alkenylpyrrolidone of the general formula

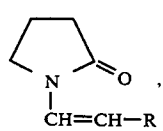

I in which R denotes hydrogen or $C_1$-$C_{20}$ alkyl,
by the reaction of an N-alkylpyrrolidone of the general formula

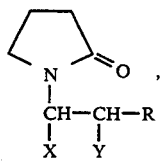

in which R has the aforementioned meanings, and X and Y stand for OH, $C_1$-$C_{20}$ alkoxy or $C_2$-$C_{20}$ alkoxycarbonyl, provided that one of the two radicals X and Y denotes hydrogen, at temperatures ranging from 200° to 600° C. and pressures ranging from 0.1 to 5 bar, in the presence of at least one acid heterogenous catalyst selected from the group consisting of
a) oxides of the elements boron, aluminum, gallium, indium, silicon, germanium, tin or lead;
b) a phosphorous acid selected from the group consisting of unsubstituted and alkyl- or aryl-substituted orthophosphorous acid, orthophosphoric acid, pyrophosphoric acid, metaphosphoric acid, polyphosphoric acids and their anhydrides;
c) a phosphorous salt selected from the group consisting of the phosphates, pyrophosphates, monohydrogen phosphates and dihydrogen phosphates of the elements of Groups IIa, IIIa, Va and the lanthanide series; and
d) an alkyl or aryl ester of an unsubstituted or alkyl- or aryl-substituted phosphoric acid or phosphorous acid.

2. A process for the preparation of an N-alkenylpyrrolidone I as claimed in claim 1, wherein an oxide of a gas phase.

3. A process for the preparation of an N-alkenylpyrrolidone I as claimed in claim 1, wherein the reaction is carried out at temperatures ranging from 250° to 500° C.

4. A process for the preparation of an N-alkenylpyrrolidone I as claimed in claim 1, wherein the reaction is carried out at temperatures ranging from 280° to 480° C.

5. A process for the preparation of an N-alkenylpyrrolidone I as claimed in claim 1, wherein the reaction is carried out over fixed bed catalysts or fluid catalysts.

6. A process as claimed in claim 1, wherein the catalyst is carried on an inert support.

7. A process as claimed in claim 1, wherein the catalyst is a dihydrogen phosphate or hydrogen phosphate of an element selected from the group consisting of Group IIa elements, vanadium and lanthanum.

8. A process as claimed in claim 7, wherein the catalyst is carried on an inert support.

9. A process as claimed in claim 1, wherein the catalyst is $SiO_2$ impregnated with phosphoric acid.

10. A process as claimed in claim 1, wherein the catalyst is $La(H_2PO_4)_3$ on diatomaceous earth.

* * * * *

UNITED STATES PATENT AND TRADEMARK OFFICE
CERTIFICATE OF CORRECTION

PATENT NO. : 5,410,070

DATED : April 25, 1995

INVENTOR(S) : Franz et al.

It is certified that error appears in the above-identified patent and that said Letters Patent is hereby corrected as shown below:

IN THE CLAIMS:

Col. 6, lines 7 and 8. after "claim 1," replace "wherein an oxide of a gas phase" with --wherein the reaction is carried out in the gas phase--.

Signed and Sealed this

Eighteenth Day of July, 1995

Attest:

BRUCE LEHMAN

Attesting Officer     Commissioner of Patents and Trademarks